(12) United States Patent
Heruth

(10) Patent No.: US 6,629,954 B1
(45) Date of Patent: Oct. 7, 2003

(54) DRUG DELIVERY PUMP WITH ISOLATED HYDRAULIC METERING

(75) Inventor: Kenneth T. Heruth, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/495,211

(22) Filed: Jan. 31, 2000

(51) Int. Cl.[7] ............................................. A61M 37/00
(52) U.S. Cl. ................................. 604/131; 604/891.1
(58) Field of Search .............................. 604/131–133, 604/140, 141, 145, 146, 890.1, 891.1, 892.1, 93.01

(56) References Cited

U.S. PATENT DOCUMENTS

| | | | |
|---|---|---|---|
| 2,972,991 A | 2/1961 | Burke | 604/110 |
| 3,572,979 A | 3/1971 | Morton | 604/151 |
| 3,966,358 A | 6/1976 | Heimes et al. | 417/12 |
| 4,265,241 A | 5/1981 | Portner et al. | 128/260 |
| 4,266,541 A | 5/1981 | Landau | 128/207.23 |
| 4,351,335 A | 9/1982 | Whitney et al. | 128/218 A |
| 4,457,752 A | 7/1984 | Vadasz | 604/135 |
| 4,581,018 A | 4/1986 | Jassawalla et al. | 604/153 |
| 4,626,243 A | 12/1986 | Singh et al. | 604/141 |
| 5,041,094 A | 8/1991 | Perego et al. | 604/143 |
| 5,290,240 A * | 3/1994 | Horres, Jr. | 128/DIG. 12 |
| 5,328,460 A * | 7/1994 | Lord et al. | 128/DIG. 12 |
| 5,348,539 A | 9/1994 | Herskowitz | 604/141 |
| 5,368,571 A * | 11/1994 | Horres, Jr. | 128/DIG. 12 |
| 5,399,166 A | 3/1995 | Laing | 604/146 |
| 5,443,450 A * | 8/1995 | Kratoska et al. | 604/141 |
| 5,458,469 A | 10/1995 | Hauser | 417/474 |
| 5,785,681 A * | 7/1998 | Indravudh | 604/65 |
| 5,810,015 A * | 9/1998 | Flaherty | 128/897 |
| 5,871,125 A * | 2/1999 | Gross | 222/207 |
| 5,976,109 A | 11/1999 | Heruth | 604/140 |
| 6,283,944 B1 * | 9/2001 | McMullen et al. | 604/142 |

FOREIGN PATENT DOCUMENTS

| | | | |
|---|---|---|---|
| DE | 40 39 191 C1 | 7/1991 | 604/891.1 |

* cited by examiner

*Primary Examiner*—Brian L. Casler
*Assistant Examiner*—Kevin C. Sirmons
(74) *Attorney, Agent, or Firm*—Eric R. Waldkoetter; John W. Albrecht

(57) ABSTRACT

A medical device and more particularly a drug delivery pump has an hydraulic reservoir, a metering device, a displacement reservoir, a drug reservoir, and a drug infusion port all contained in a housing that can either be attached to or implanted into a patient. The hydraulic reservoir contains an hydraulic fluid that is under compression and flows through the metering device at an hydraulic rate. The hydraulic metering is isolated from the drug, and the metering device does not contain moving parts. The hydraulic fluid then flows into the displacement reservoir that applies pressure to the drug reservoir. The drug reservoir is compressible and adapted to contain a drug. As the drug reservoir is compressed, drug egresses through the drug infusion port at an infusion rate that is controlled by hydraulic rate. A method for filling the drug pump and a method for infusing drug from the drug pump are also disclosed.

20 Claims, 4 Drawing Sheets

DRUG DELIVERY PUMP WITH ISOLATED HYDRAULIC METERING

BACKGROUND OF THE INVENTION

A medical device is disclosed and more specifically a drug delivery pump either attached to or implanted into a patient that infuses a therapeutic substance.

The medical device industry produces a wide variety of electronic and mechanical devices for treating patient medical conditions. Depending upon the medical condition, medical devices can be surgically implanted, connected externally to the patient receiving treatment, or used during surgery. Clinicians use medical devices alone or in combination with drug therapies and surgery to treat patient medical conditions. For some medical conditions, medical devices provide the best, and sometimes the only, therapy to restore an individual to a more healthful condition and a fuller life. One type of medical device is a drug delivery pump.

A drug delivery pump can be attached to or implanted into a patient, and it infuses a therapeutic agent such as a drug or infusate at a predetermined infusion rate and location to treat a condition such as pain, spasticity, or other medical conditions. Drug delivery pumps use a metering device to measure the amount of drug being infused. Some metering devices directly meter the drug being infused by passing the drug through a flow restriction. Since drugs typically have a viscosity about that of water, the flow restriction is often very small to achieve an appropriate infusion rate. Small flow restrictions are difficult to manufacture, prone to clogging, and can apply shear forces to the drug being metered. In addition to flow restriction, there are also other complex direct or indirect metering devices. These complex devices can require significant residential space, battery power, and moving parts such as pumps, gears and other actuators that can be found in peristaltic pumps, electrically operated valves and pumps, and microelectromechanical machined (MEMs) components. Complex metering devices are more expensive to manufacture than simpler devices and can be less reliable and less safe due to their complexity, susceptibility to clogging, alteration of the drug being infused, and creation of significant drug dead space. A less complex, safer, reliable, and low cost metering system is desirable.

SUMMARY OF THE INVENTION

A drug delivery pump has an hydraulic metering system that is isolated from the drug. The drug delivery pump has an hydraulic reservoir that is disposed in a housing for containing an hydraulic fluid. A metering device without moving parts is in fluid contact with the hydraulic reservoir and controls the rate that the hydraulic fluid flows from the hydraulic reservoir into a displacement reservoir. The displacement reservoir receives the hydraulic fluid flowing through the metering device, and the displacement reservoir applies pressure to compress a drug reservoir. The drug reservoir is compressible and designed to contain a therapeutic substance such as a drug. A drug infusion port is coupled to the drug reservoir and when the drug reservoir is compressed the therapeutic substance is infused through the drug infusion port.

In another aspect of the invention, the drug delivery pump with hydraulic metering is filled by inserting a filling device containing drug into a drug fill port. Drug fills the drug reservoir and compresses hydraulic fluid in a displacement reservoir. The compressed hydraulic fluid raises pressure in the displacement reservoir which opens a relief valve between the displacement reservoir and the hydraulic reservoir. Hydraulic fluid flows from the displacement reservoir into the hydraulic reservoir. Once the displacement reservoir pressure is below the relief valve relief pressure, the relief valve closes. In still another aspect of the invention, the drug pump begins operation by compressing the hydraulic reservoir causing hydraulic fluid to flow into a metering device. Hydraulic fluid flow is metered to control its flow rate as the hydraulic fluid flows through the metering device and fills the displacement reservoir. The displacement reservoir then applies pressure to the drug reservoir compressing the drug reservoir. Drug is infused as the drug reservoir is compressed.

DETAILED DESCRIPTION OF THE PREFERRED EMBODIMENTS

Figure 1:
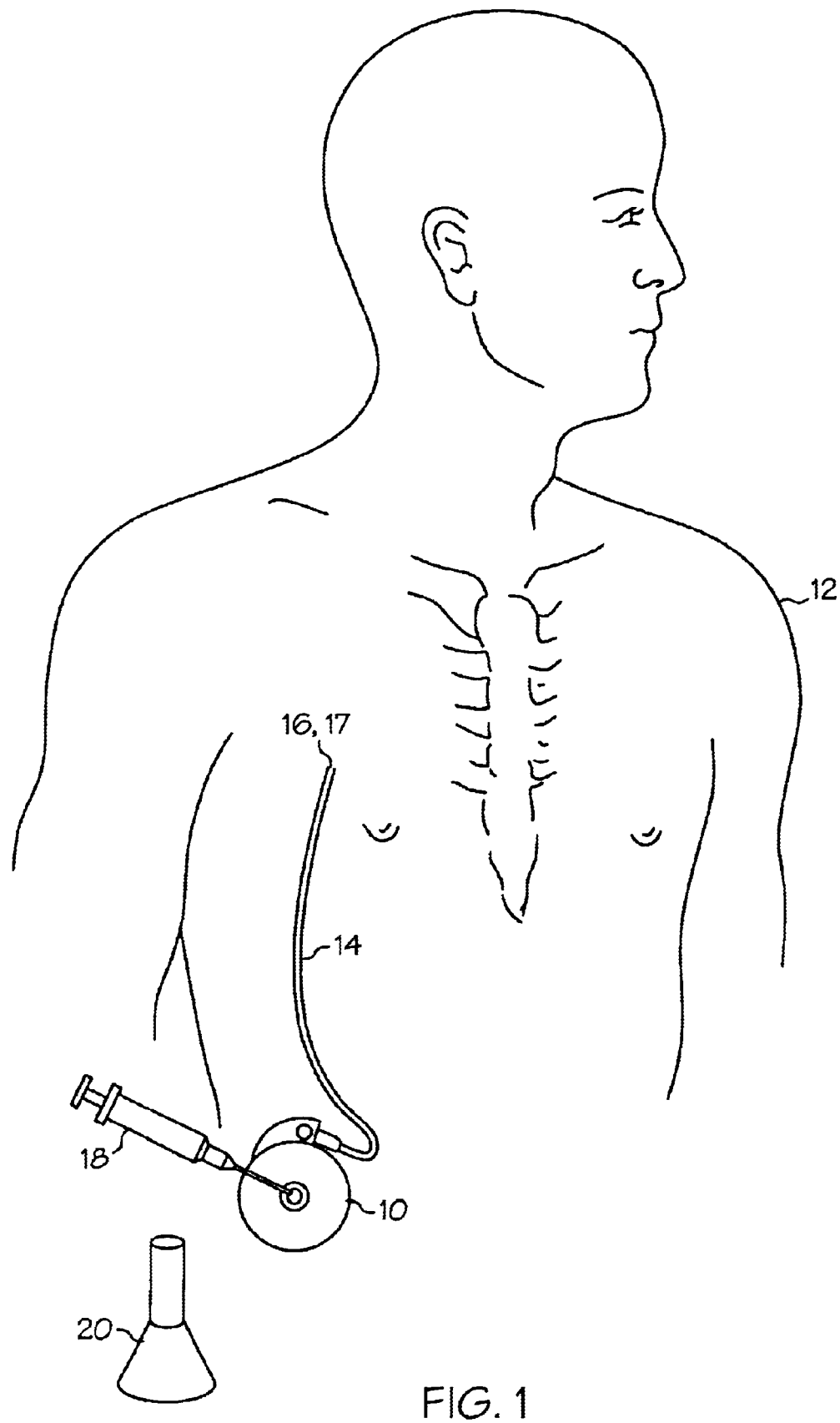
FIG. 1 shows an environment of an drug delivery pump with isolated hydraulic metering.

FIG. 1 shows the general environment of a drug delivery pump 10 with isolated hydraulic metering that can either be attached to or implanted into a patient 12. When implanted, the drug delivery pump 10 is typically implanted subcutaneous in the patient 12 with a drug delivery catheter 14 positioned to deliver a drug 16, also known as a therapeutic substance, to a selected location at a predetermined infusion rate 17. A fill device 18 such as a syringe is typically used to access the drug delivery pump 10 for filling and refilling. A wide variety of drugs 16 are compatible with the drug delivery pump 10 such as morphine sulfate or baclofen. Drugs 16 typically have a viscosity from about 0.1 to 10.0 centipoise at body temperature with many drugs 16 having the viscosity of water which is about 0.7 centipoise at body temperature. The hydraulic fluid 20 is selected for its flow characteristics typically with a viscosity in the range from about 100.0 to 1,000.0 centipoise. A wide variety of hydraulic fluids 20 can be using in the drug delivery pump 10 such as castor oil, glycerin, and silicone oil. The drug delivery pump 10 can be filled with hydraulic fluid 20 either before being filled with the drug 16 or after being filled with the drug 16. The infusion rate 17 can be changed simply by varying the viscosity of the hydraulic fluid. The following figures and description provide more detailed information about the drug delivery pump 10.

Figure 2:
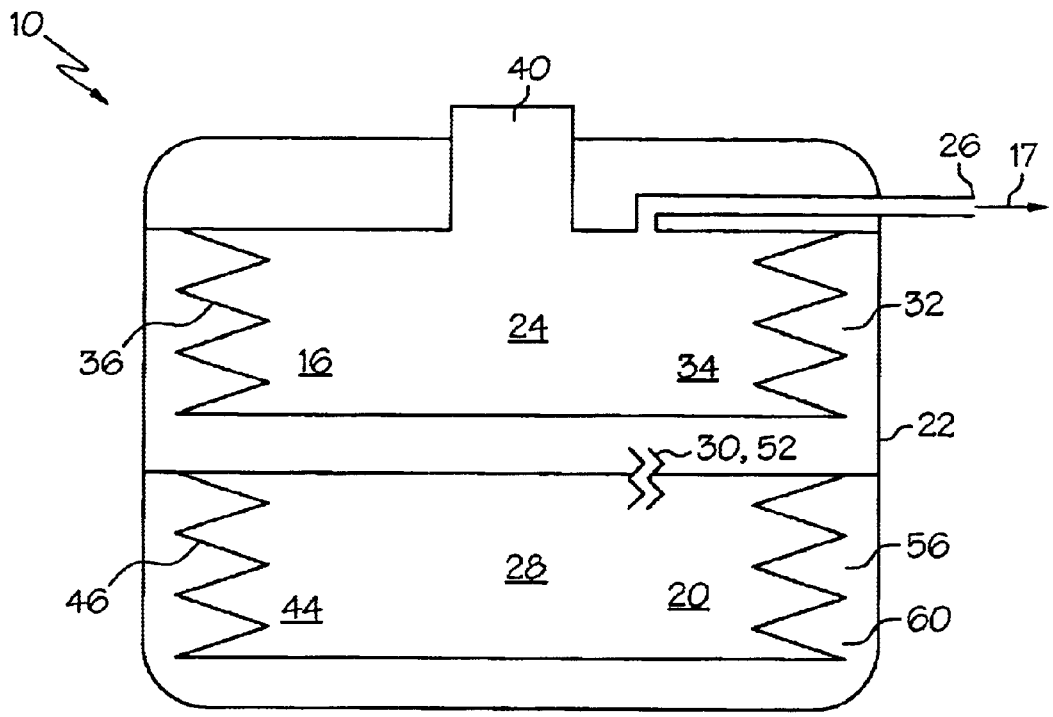
FIG. 2 shows a block diagram of the drug delivery pump.
Figure 3:
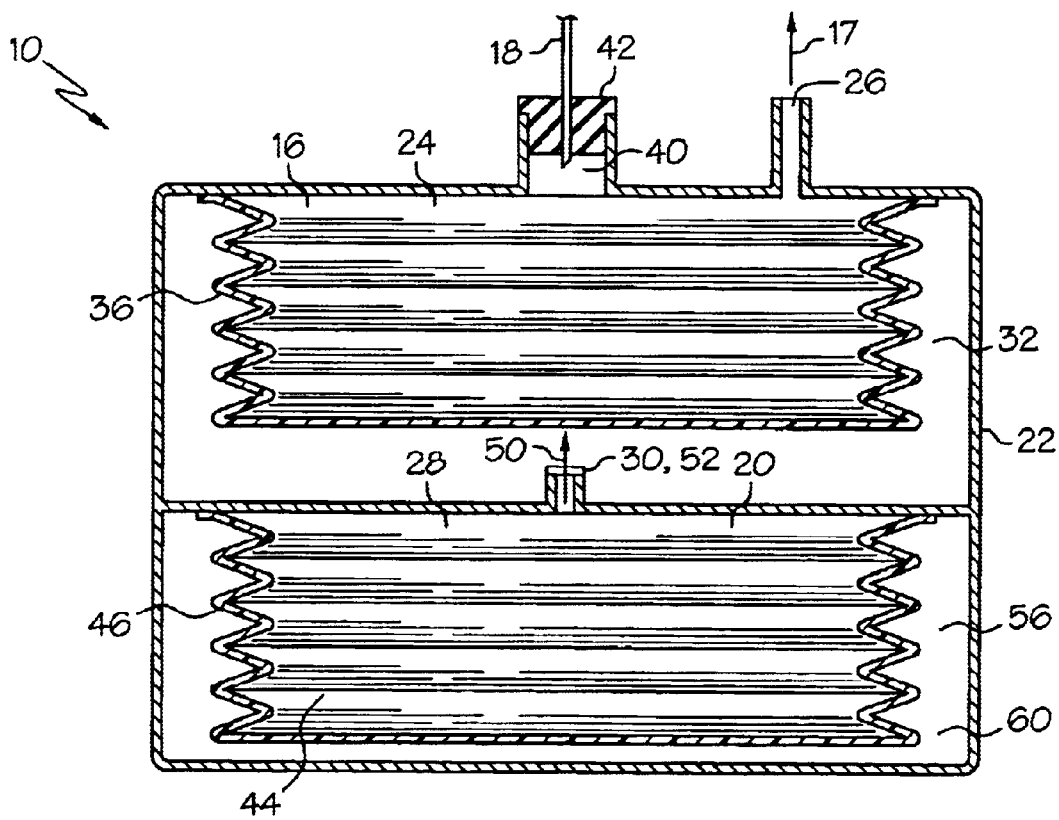
FIG. 3 shows an embodiment of the drug delivery pump.

FIG. 2 shows a block diagram of a drug delivery pump 10 with isolated hydraulic metering, and FIG. 3 shows a corresponding embodiment. The drug delivery pump 10 includes a housing 22, a drug reservoir 24, a drug infusion port 26, an hydraulic reservoir 28, a metering device 30, and a displacement reservoir 32. The housing 22 can be a single housing 22 as shown or the housing 22 can include separate sub-housings that are coupled together. For example, the drug reservoir 24 and the hydraulic-reservoir 28 can be in separate housings coupled together with a tube that permits hydraulic fluid 20 to flow into the displacement reservoir 32 which is co-located with the drug reservoir 24. The housing 22 is manufactured from a material compatible with being attached to or implanted into a patient 12 such as titanium. Disposed in the housing 22 is the drug reservoir 24.

The drug reservoir 24 is a compressible structure that is adapted to contain a drug 16. The drug reservoir 24 has a drug reservoir interior 34, drug reservoir exterior 36, a drug infusion port 26, a drug fill port 40, and a septum 42. The drug infusion port 26 is coupled to the drug reservoir 24 and extends through the housing 22, so the drug 16 can egress from the drug reservoir interior 34 though the drug infusion port 26 into the drug delivery catheter 14 (FIG. 1). The drug fill port 40 is coupled to the drug reservoir 24 and also extends through the housing 22, so the drug 16 can ingress, typically from a syringe 18, from outside the housing 22 into the drug reservoir interior 34. The septum 42 carried on the housing 22 is coupled to the drug fill port 40 and provides one-way fluid coupling between the drug fill port 40 and outside the housing 22. In some versions of the drug delivery pump 10, the drug fill port 40 and septum 42 can be omitted if the drug delivery pump 10 is filled during manufacturing with the drug 16, and the drug delivery pump 10 is not intended to be refilled. In other versions, the drug fill port 40 and the septum 42 can be integral. The drug fill port 40, drug reservoir interior 34 and the infusion port 26 are manufactured from a material that is non-reactive to the drug, so the drug 16 is only exposed to the non-reactive material when delivered. Since the drug 16 is only exposed to a non-reactive material during storage and delivery, some drugs. 16 will be more effective, longer lasting, and safer because the drugs 16 are not altered by a reactive material. The non-reactive material can be a material such as titanium, stainless steel, platinum, or gold. The drug reservoir exterior 36 can be manufactured from a material that is compatible with the hydraulic fluid 20. The drug reservoir 24 can take a variety of shapes including a bellows, diaphragm, bladder, or cylinder. Also disposed in the housing 22 is the hydraulic reservoir 28.

Figure 4:
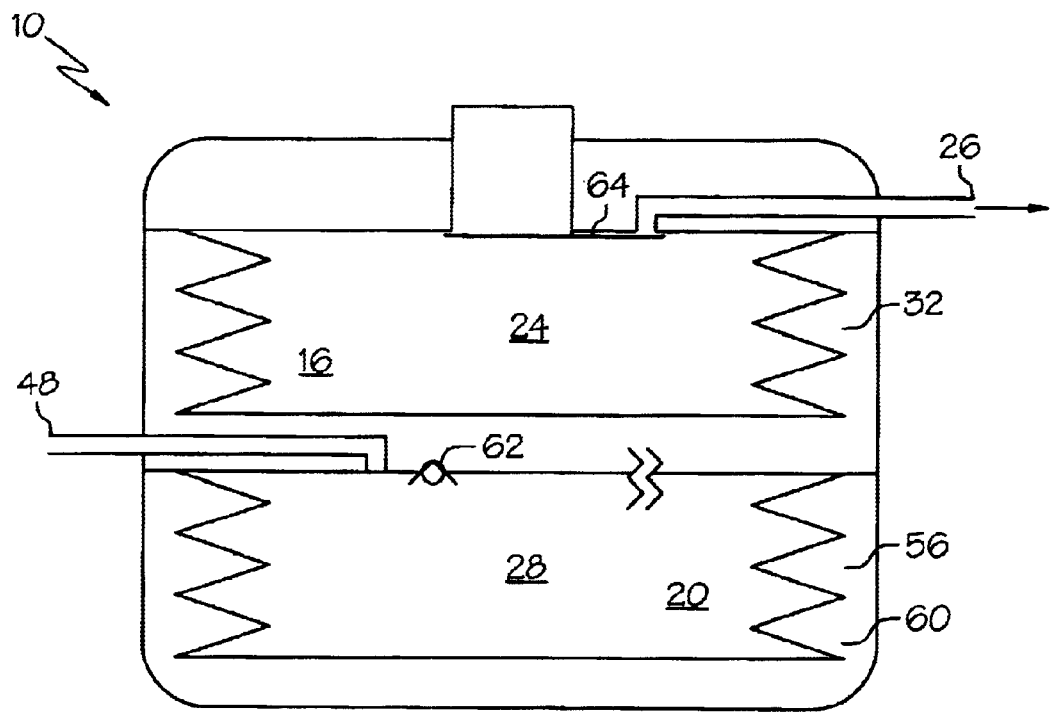
FIG. 4 shows another block diagram of the drug delivery pump.
Figure 5:
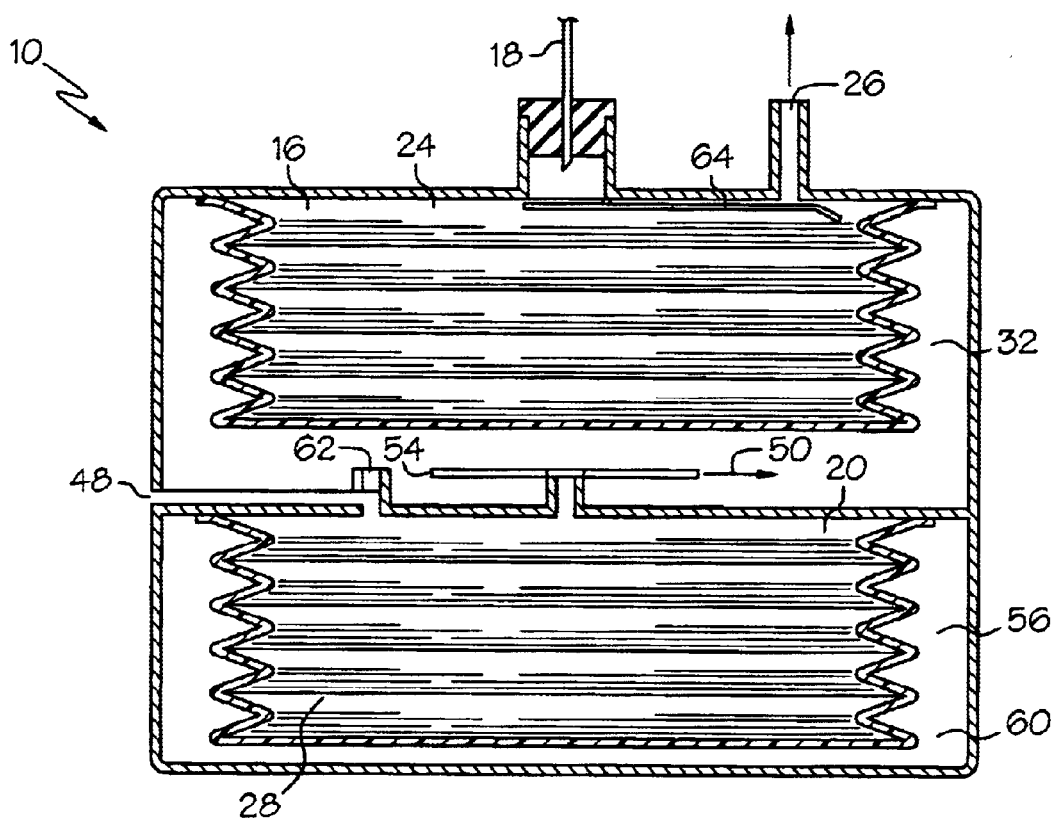
FIG. 5 shows another embodiment of the drug delivery pump.

The hydraulic reservoir 28 is a compressible structure adapted to contain the hydraulic fluid 20. The hydraulic reservoir 28 has an hydraulic reservoir interior 44, an hydraulic reservoir exterior 46, and an hydraulic fill port 48 (FIGS. 4–5). The hydraulic reservoir interior 44 is manufactured from a material that is compatible with the hydraulic fluid 20. In some versions of the drug delivery pump 10, the hydraulic fill port 48 is coupled to the hydraulic reservoir 28 for filling the hydraulic reservoir 28 with hydraulic fluid 20. The hydraulic fill port 48 is either equipped with a one-way valve or sealed once the hydraulic reservoir 28 is filled. The hydraulic fill port 48 can be fitted with a septum to permit changing hydraulic fluid 20 viscosity and thereby the predetermined infusion rate 17 while the drug delivery pump 10 is implanted. The hydraulic fill port 48 (FIGS. 4–5) can be omitted if the hydraulic reservoir 28 is only filled once during manufacturing. The hydraulic fluid 20 has a viscosity selected to cooperate with the metering device 30 to cause the drug 16 to be delivered at a predetermined infusion rate 17. When the hydraulic reservoir 28 is filled with the hydraulic fluid 20, the hydraulic fluid 20 is compressed by the hydraulic reservoir 28. The hydraulic reservoir 28 can exert compressive force on the hydraulic fluid 20 by its geometry and material composition such as a bellows that is annealed so that in its relaxed state the bellows is collapsed. The hydraulic reservoir 28 can also be compressed by the elastomeric properties of a bladder or by an external force such as a spring or a propellant. The hydraulic reservoir 28 can take a variety of shapes such as a bellows, diaphragm, bladder, or cylinder. Coupled to the hydraulic reservoir 28 is the metering device 30.

The metering device 30 without moving parts is in fluid contact with both the hydraulic reservoir interior 44 and the displacement reservoir 32. The metering device 30 dispenses the hydraulic fluid 20 from the hydraulic reservoir 28 into the displacement reservoir 32 at a predetermined hydraulic rate 50. The metering device 30 is selected to cooperate with the hydraulic fluid 20 to dispense the drug 16 at a predetermined infusion rate 17. With a given metering device 30, the predetermined infusion rate 17 can be adjusted by varying the viscosity of the hydraulic fluid 20. By adjusting the predetermined infusion rate 17 with the hydraulic fluid's 20 viscosity, a single metering device 30 can be used for a wide range of applications to improve versatility of the drug delivery pump 10 and reduce manufacturing costs. A variety of metering devices 30 can be used such as a flow restriction 52 with a continuous flow path in the form of a capillary tube 54 (FIG. 5). When the metering device 30 is a capillary tube 54 with a circular cross-section the flow rate can be calculated with the equation:

$$Q = \frac{\pi D^4 \Delta P}{128 L \mu};$$

where $Q$=Flow, $D$=Diameter, $P$=Pressure drop, $L$=Length, and $\mu$=Viscosity.

Since the hydraulic rate 50 is a function of both the flow restriction 52 and the viscosity of the hydraulic fluid 20, the flow restriction 52 can often have a larger diameter than the size of a flow restriction 52 used to directly meter a drug 16 because the hydraulic fluid 20 can have a viscosity selected that is substantially higher than the drug 16. When a capillary tube 54 is used as the flow restriction 52, the capillary tube 54 can have both a larger diameter and a shorter length than a capillary tube 54 used with a lower viscosity fluid than the hydraulic fluid 20. A capillary tube 54 that is shorter and has a larger diameter is typically less costly to manufacture, easier to install, more dimensionally stable, and less likely to clog. Capillary tubes 54 used for a metering device 30 will typically have an inside diameter in the range from about 0.000254 cm (0.00001 in) to about 0.0254 cm (0.01 in). To better understand the advantage of hydraulic metering using a higher viscosity fluid than typical drugs 16, consider the following examples.

When using a typical drug 16 for metering, a capillary tube 54 configured to achieve a flow rate of approximately 1.1 ml/day with a drug 16 having the viscosity of water about 0.7 centipoise that is under a pressure of 0.276 bar (4.0 psi) would have a diameter of 0.0254 cm (0.01 in) and a length of 200.0 cm (79.0 in). In contrast, when using a typical hydraulic fluid 20, a capillary tube 54 with the a diameter of 0.058 cm (0.02 in) used with a hydraulic fluid 20 such as castor oil or glycerin both having a viscosity of about 285.0 centipoise that is under a pressure of 0.276 bar (4.0 psi) would require a length of only 8.0 cm (3.1 in) to achieve a flow rate of approximately 1.1 ml/day. Shorter precision capillary tubes 54 are less likely to clog, safer, require less residential space, easier to manufacture and less costly. Since only the hydraulic fluid 20 contacts the metering device 30, the opportunity for clogging is reduced. The metering device 30 is less likely to clog because contamination in the drug reservoir 24, such as from tissue and septum 42 material introduced into the drug reservoir 24 when a syringe 18 is inserted to refill the drug pump 10, does not contact the metering device 30. Since metering is not dependent on the drug 16, a wide variety of drugs 16 can be used without requiring changes to the metering device 30. The flexibility to use a wide variety of drugs 16 allows the clinician greater flexibility in selecting a therapy appropriate for the patient 12. Hydraulic fluid 20 flows through the metering device 30 into the displacement reservoir 32.

The displacement reservoir 32 is in fluid contact with the metering device 30. The displacement reservoir 32 can take a variety of shapes and structures such as a bellows, diaphragm, or cylinder. In some versions, the displacement reservoir 32 will be residential space in the housing 22 surrounding the drug reservoir 24 that is partitioned from the hydraulic reservoir 28. When the displacement reservoir 32 receives hydraulic fluid 20 flowing through the metering device 30, the displacement reservoir 32 applies pressure to the drug reservoir 24. The displacement reservoir 32 applies pressure to the drug reservoir 24 by either containing the hydraulic fluid 20 flow and generating mechanical movement that is used to compress the drug reservoir 24 or by containing the hydraulic fluid 20 flow and generating a compressive force that is applied to the drug reservoir 24. Under pressure from the displacement reservoir 32, the drug reservoir 24 begins infusing the drug 16 through the drug infusion port 26. When the hydraulic reservoir 28 compresses, an hydraulic reservoir space 56 is created in the drug delivery pump 10 which can create a lower pressure that can interfere with operation of the hydraulic reservoir 28. To compensate for the lower pressure generated in the hydraulic reservoir space 56, some versions of the drug pump 10 include a propellant reservoir 58 that is disposed in the housing 22. The propellant reservoir 58 communicates with the hydraulic reservoir 28 to fill the hydraulic reservoir space 56 created when the hydraulic reservoir 28 collapses when dispensing hydraulic fluid 20. The propellant reservoir 58 contains a propellant 60 that changes phase from a liquid to a vapor while maintaining substantially constant pressure. The propellant 60 is a fluid that will change phase to a vapor at body temperature such as some refrigerants. In some versions of the drug delivery pump 10, hydraulic fluid 20 flow from the displacement reservoir 32 into the hydraulic reservoir 28 during filling and refilling is controlled by a relief valve 62.

FIG. 4 shows a block diagram of another version of the drug delivery pump 10 and FIG. 5 shows a corresponding embodiment. Some versions of the drug pump 10 can have a relief valve 62 to provide one-way fluid coupling from the displacement reservoir 32 into the hydraulic reservoir 28. The relief valve 62 has a relief pressure that is greater than the propellant 60 vapor pressure but less than the pressure exerted on the displacement reservoir 32 when the drug reservoir 24 is refilled, so the relief valve 62 will open and allow hydraulic fluid 20 to return to the hydraulic reservoir 28 during filling and refilling. In addition to the relief valve 62, some versions can also have an infusion valve 64.

The infusion valve 64 substantially prevents infusion during filling and refilling. The infusion valve 64 can be closed before the drug reservoir 24 is refilled to prevent drug 16 from flowing from the drug reservoir 24 through the infusion port 26 when refilling temporarily raises the pressure in the drug reservoir 24. The syringe 18 needle can be used to directly actuate and close the infusion valve 64 when the syringe 18 is used to refill the drug reservoir 24. The infusion valve 64 can be a wide variety of valves that can be actuated to substantially close the infusion port 26 and then actuated to open the infusion port 26 such as a lever valve that is biased open and can be actuated by the syringe 18 needle during filling and refilling to close the infusion valve 64. The infusion valve 64 can be manufactured from a non-reactive material such as used for the infusion port 26. The drug delivery pump 10 can be better understood by considering its operation.

Figure 6:
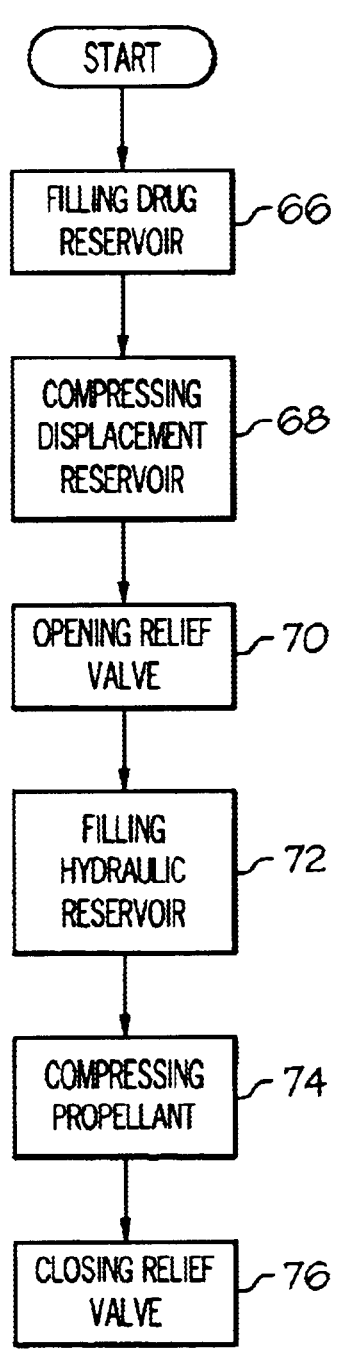
FIG. 6 shows a method for filling the drug delivery pump.

FIG. 6 shows a flow diagram of a method for filling the drug delivery pump 10 with hydraulic metering. Filling the drug reservoir 66 occurs by inserting a filling device 18, such as a syringe with needle, into the drug fill port 40 that is connected to the drug reservoir 24. In versions with a septum 42 connected to the drug fill port 40, the needle will be inserted through the septum 40. The drug reservoir 24 begins filling with drug 16 dispensed from the filling device 18 through the drug fill port 40 into the drug reservoir 24. In some versions, an infusion valve 64 typically actuated by the syringe needle will be used to prevent infusion during filling and refilling. Compressing the displacement reservoir 68 occurs as the drug reservoir 24 fills. The expanding drug reservoir 24 compresses the hydraulic fluid 20 contained in the displacement reservoir 32. Opening the relief valve 70 occurs when the compressed hydraulic fluid 20 exceeds the relief pressure of the relief valve 62, causing the relief valve 62 to open. Filling the hydraulic reservoir 72 occurs as the open relief valve 62 permits hydraulic fluid 20 to move from the displacement reservoir 32 into the hydraulic reservoir 28. Compressing the propellant 74 occurs as the hydraulic reservoir 28 fills, and the hydraulic reservoir space 56 decreases causing the propellant 60 to compress. Under this compression, some propellants 60 will change phase from a vapor to a liquid while substantially maintaining a constant pressure. Closing the relief valve 76 occurs once the drug reservoir 24 is filled and the relief valve 62 closes. The relief valve 62 closes because the hydraulic fluid 20 pressure in the displacement reservoir 32 no longer exceeds the relief pressure. The filling device 18 is removed from the drug fill port 40. The filled drug delivery pump 10 can now begin the process to infuse the drug 16 using isolated hydraulic metering.

Figure 7:
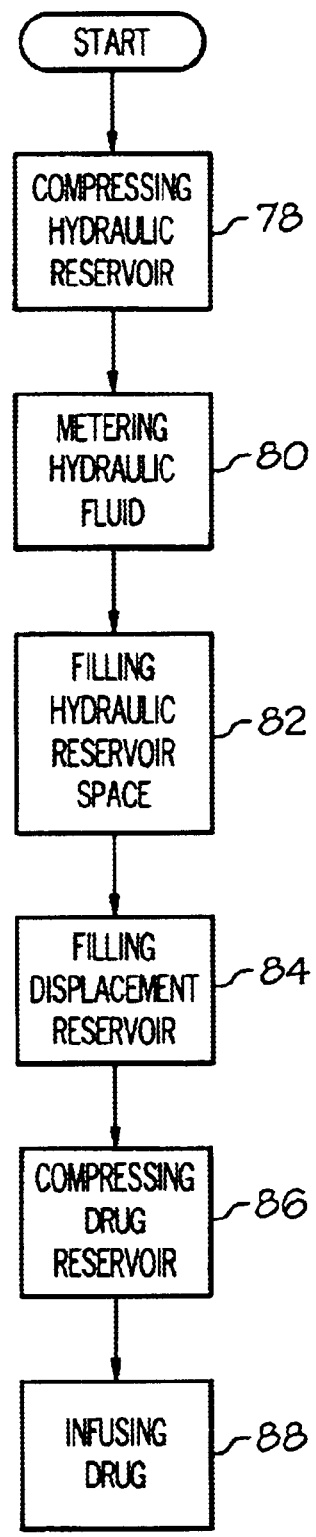
FIG. 7 shows a method of operating the drug delivery pump.

FIG. 7 shows a flow diagram of a method for hydraulic metering for a drug delivery pump 10. Compressing the hydraulic reservoir 78 occurs as the hydraulic reservoir 28 is compressed under a force such as the hydraulic reservoir 28 structure or propellant 60. Metering the hydraulic fluid 80 occurs as the hydraulic fluid 20 flows through the metering device 30 into the displacement reservoir 32. Filling the hydraulic reservoir space 82 occurs as the hydraulic reservoir space 56 created by the collapsing hydraulic reservoir 28 is filled by the propellant 60 to avoid creation of a low-pressure area in the hydraulic reservoir space 56 that could interfere with hydraulic reservoir 28 operation. Filling the displacement reservoir 84 occurs as the as hydraulic fluid 20 flows from the hydraulic reservoir 28 through the metering device 30 into the displacement reservoir 32. Compressing the drug reservoir 86 occurs as displacement reservoir 32 applies pressure to the drug reservoir 24. Infusing the drug 88 occurs as the compressing drug reservoir 24 expels drug 16 through the drug infusion port 26. Since the metering device 30 can be configured so the drug 16 flows in substantially a laminar flow, the drug 16 is not subjected to shear forces that can degrade some drugs 16 such as insulin.

Although the invention has been described in detail with reference to certain preferred versions, other versions are possible. Therefore the spirit and scope of the appended claims should not be limited to the description of the preferred versions described in this disclosure.

What is claimed is:

1. A drug delivery pump with isolated hydraulic metering comprising:
   a housing compatible with a human body;
   a drug reservoir disposed in the housing, the drug reservoir having a drug reservoir interior and the drug reservoir being compressible and adapted to contain a drug;
   a drug infusion port coupled to the drug reservoir extending through the housing, the drug infusion port providing for drug egress from the drug reservoir interior though the housing,
   an hydraulic reservoir disposed in the housing, the hydraulic reservoir having an hydraulic reservoir interior, and the hydraulic reservoir being adapted to contain hydraulic fluid;
   a metering device without moving parts, wherein the metering device is a capillary tube in fluid contact with the hydraulic reservoir interior, the capillary tube controlling the rate that the hydraulic fluid flows from the hydraulic reservoir; and
   a displacement reservoir in fluid contact with the capillary tube, the displacement reservoir receiving the hydraulic fluid flowing though the capillary tube and the displacement reservoir applying pressure to compress the drug reservoir which dispenses the drug at a predetermined infusion rate through the drug infusion port; wherein the capillary tube has an inside diameter in the range from about 0.000254 cm to about 0.0254 cm.

2. A drug delivery pump with isolated hydraulic metering, comprising:
   a housing compatible with a human body;
   a drug reservoir disposed in the housing, the drug reservoir having a drug reservoir interior and the drug reservoir being compressible and adapted to contain a drug;
   a drug infusion port coupled to the drug reservoir extending through the housing, the drug infusion port providing for drug egress from the drug reservoir interior though the housing;
   an hydraulic reservoir disposed in the housings the hydraulic reservoir having an hydraulic reservoir interior, and the hydraulic reservoir being adapted to contain hydraulic fluid;
   a metering device without moving parts, wherein the metering device is a capillary tube in fluid contact with the hydraulic reservoir interior, the capillary tube controlling the rate that the hydraulic fluid flows from the hydraulic reservoir; and
   a displacement reservoir in fluid contact with the capillary tube, the displacement reservoir receiving the hydraulic fluid flowing though the capillary tube and the displacement reservoir applying pressure to compress the drug reservoir which dispenses the drug at a predetermined infusion rate through the drug infusion port; wherein the capillary tube has a length in the range from about 0.05 cm to about 5.0 cm.

3. A drug delivery pump with isolated hydraulic metering, comprising:
   a housing compatible with a human body;
   a drug reservoir disposed in the housing, the drug reservoir having a drug reservoir interior and the drug reservoir being compressible and adapted to contain a drug;
   a drug infusion port coupled to the drug reservoir extending through the housing, the drug infusion port providing for drug egress from the drug reservoir interior though the housing;
   an hydraulic reservoir disposed in the housing, the hydraulic reservoir having an hydraulic reservoir interior, and the hydraulic reservoir being adapted to contain hydraulic fluid;
   a metering device without moving parts in fluid contact with the hydraulic reservoir interior, the metering device controlling the rate that the hydraulic fluid flows from the hydraulic reservoir; and
   a displacement reservoir in fluid contact with the metering device, the displacement reservoir receiving the hydraulic fluid flowing though the metering device and the displacement reservoir applying pressure to compress the drug reservoir which dispenses the drug at a predetermined infusion rate through the drug infusion port;
   wherein the displacement reservoir is residential space in the housing surrounding the drug reservoir.

4. An drug delivery pump with isolated hydraulic metering, comprising:
   a housing compatible a human body;
   a drug reservoir disposed in the housing, the drug reservoir having a drug reservoir interior and the drug reservoir being compressible and adapted to contain a drug;
   a drug infusion port coupled to the drug reservoir extending through the housing, the drug infusion port providing for drug egress from the drug reservoir interior through the housing;
   means for hydraulic fluid containment disposed in the housing, the means for hydraulic fluid containment having an hydraulic containment interior,
   and the means for hydraulic fluid containment being adapted to contain an hydraulic fluid;
   means for metering without moving parts in fluid contact with the hydraulic containment interior, the means for metering controlling the rate that the hydraulic fluid flows from the means for hydraulic containment; and,
   means for displacement containment in fluid contact with the means for metering, the means for displacement containment receiving the hydraulic fluid flowing through the means for metering and the means for displacement containment applying pressure to the drug reservoir which infuses the drug at a predetermined infusion rate through the drug infusion port.

5. The drug delivery pump as in claim 4 wherein the predetermined dispense rate is a function of both the means for metering and the hydraulic fluid's flow characteristics.

6. The drug delivery pump as in claim 4 wherein the predetermined dispense rate is changed by varying only the hydraulic fluid's flow characteristics.

7. The drug delivery pump as in claim 4 wherein the means for metering provides a continuous flow path.

8. An isolated hydraulic metering system for a drug delivery pump, comprising:
   means for hydraulic containment for receiving an hydraulic fluid;
   means for metering without moving parts fluidly coupled to the means for hydraulic containment for dispensing the hydraulic fluid from the means for hydraulic containment at a predetermined hydraulic rate; and,
   means for displacement containment fluidly coupled to the means for metering for receiving the hydraulic fluid flowing through the means for metering at the predetermined hydraulic rate for compressing a drug reservoir to dispense a drug at a predetermined dispense rate.

9. The drug delivery pump as in claim 8 wherein the predetermined hydraulic rate is a function of both the means for metering and the hydraulic fluid's flow characteristics.

10. The drug delivery pump as in claim 8 wherein the predetermined dispense rate is changed by varying only the hydraulic fluid's flow characteristics.

11. The drug delivery pump as in claim 8 wherein the means for metering provides a continuous flow path.

12. A method for filling a drug delivery pump with hydraulic metering comprising:

inserting a filling device containing drug through a drug fill port;

filling a drug reservoir with a drug dispensed from the filling device through the drug fill port into the drug reservoir;

compressing hydraulic fluid contained in a displacement reservoir with the drug reservoir as the drug reservoir expands when being filled;

opening a relief valve when the pressure of the compressed hydraulic fluid exceeds the relief pressure of the relief valve;

filling an hydraulic reservoir with hydraulic fluid flowing from the displacement reservoir through the relief valve into the hydraulic reservoir;

closing the relief valve when the pressure of the hydraulic fluid outside the hydraulic reservoir is less than the relief pressure.

13. The method of filling a drug delivery pump as in claim 12, further comprising closing a infusion valve to stop drug flow from the drug reservoir through an infusion port while filling the drug reservoir.

14. The method of filling a drug delivery pump as in claim 12, comprising compressing propellant contained in a hydraulic reservoir space when the hydraulic reservoir hydraulic fluid.

15. A drug delivery pump with isolated hydraulic metering, comprising:

a housing compatible with a human body;

a compressible drug reservoir disposed within the housing, the drug reservoir adapted to contain a drug;

a drug infusion port in fluid contact with the drug reservoir and extending through the housing such that the drug can egress the drug reservoir when the drug reservoir is compressed;

a compressible hydraulic reservoir disposed within the housing, the hydraulic reservoir adapted to contain and to dispense a hydraulic fluid when the hydraulic reservoir is compressed;

a metering device without moving parts in fluid contact with hydraulic reservoir to control the rate that the hydraulic fluid flows from the hydraulic reservoir;

a displacement reservoir in fluid contact with the metering device, the displacement reservoir receiving hydraulic fluid dispensed from the hydraulic reservoir through the metering device such that filling the displacement reservoir compresses the drug reservoir; and a propellant reservoir coupled to the hydraulic reservoir and adapted to contain a fluid propellant, wherein expansion of the fluid propellant compresses the hydraulic reservoir.

16. The drug delivery pump as in claim 15 wherein at least one of the drug reservoir and the hydraulic reservoir includes one of the group consisting of a bellows, a diaphragm a bladder, and a cylinder.

17. The drug delivery pump of claim 15 wherein the drug includes a viscosity in the range of 0.1 to 10.0 centipoise at body temperature and the hydraulic fluid has a viscosity in the range of 100.0 to 1000.0 centipoise at body temperature.

18. The drug delivery pump as in claim 15 wherein the metering device includes a capillary tube.

19. The drug delivery pump as in claim 15 wherein the displacement reservoir is disposed within the housing such that hydraulic fluid is in direct contact with the drug reservoir but isolated from the drug.

20. The drug delivery pump as in claim 15 wherein the propellant reservoir is disposed within the housing such that the fluid propellant is in direct contact with the hydraulic reservoir but the fluid propellant is isolated from the hydraulic fluid.

* * * * *

UNITED STATES PATENT AND TRADEMARK OFFICE
CERTIFICATE OF CORRECTION

PATENT NO. : 6,629,954 B1
DATED : October 7, 2003
INVENTOR(S) : Heruth

It is certified that error appears in the above-identified patent and that said Letters Patent is hereby corrected as shown below:

<u>Title page,</u>
Item [57], ABSTRACT,
Lines 2, 6 and 7, "an hydraulic" should be -- a hydraulic --.

<u>Column 7,</u>
Line 14, "an hydraulic" should be -- a hydraulic --.
Lines 24 and 53, "flowing though the" should be -- flowing through the --.
Line 40, "though the" should be -- through the --.
Line 41, "housings" should be -- housing --.

<u>Column 8,</u>
Lines 3, 26 and 34, "an hydraulic" should be -- a hydraulic --.
Line 13, "flowing though the" should be -- flowing through the --.

<u>Column 9,</u>
Line 38, "reservoir hydraulic fluid" should be -- reservoir fills with hydraulic fluid --.

<u>Column 10,</u>
Line 25, "a diaphragm a blader" should be -- a diaphragm, a bladder --.

Signed and Sealed this

Fifteenth Day of November, 2005

JON W. DUDAS
*Director of the United States Patent and Trademark Office*